(12) United States Patent
Rigatti et al.

(10) Patent No.: US 10,604,800 B2
(45) Date of Patent: Mar. 31, 2020

(54) METHODS OF INCREASING SEQUENCING ACCURACY

(71) Applicant: Illumina Cambridge Limited, Nr. Saffron Walden, Essex (GB)

(72) Inventors: Roberto Rigatti, Nr. Saffron Walden (GB); Jonathan Mark Boutell, Nr. Saffron Walden (GB)

(73) Assignee: Illumina Cambridge Limited, Nr. Saffron Walden, Essex (GB)

( * ) Notice: Subject to any disclaimer, the term of this patent is extended or adjusted under 35 U.S.C. 154(b) by 145 days.

(21) Appl. No.: 15/317,623

(22) PCT Filed: Jun. 12, 2015

(86) PCT No.: PCT/GB2015/051736
§ 371 (c)(1),
(2) Date: Dec. 9, 2016

(87) PCT Pub. No.: WO2015/189637
PCT Pub. Date: Dec. 17, 2015

(65) Prior Publication Data
US 2017/0137876 A1    May 18, 2017

(30) Foreign Application Priority Data
Jun. 14, 2014 (GB) .................................. 1410646.2

(51) Int. Cl.
*C12Q 1/6869* (2018.01)
*C12Q 1/6844* (2018.01)
*C12P 19/34* (2006.01)

(52) U.S. Cl.
CPC ......... *C12Q 1/6869* (2013.01); *C12Q 1/6844* (2013.01)

(58) Field of Classification Search
None
See application file for complete search history.

(56) References Cited

U.S. PATENT DOCUMENTS 6,300,070 B1 *  10/2001  Boles .................. C12Q 1/6834
                                                    435/6.11
6,514,706 B1 *  2/2003   Von Kalle ........... C12Q 1/6855
                                                    435/6.12
(Continued)

FOREIGN PATENT DOCUMENTS

WO    WO 1998/44151    10/1998
WO    WO2002/059353    8/2002
(Continued)

OTHER PUBLICATIONS

Ma et al., "Isothermal amplification method for next-generation sequencing," Aug., vol. 110, No. 35, pp. 14320-14323 (Year: 2013).*

(Continued)

*Primary Examiner* — Young J Kim
(74) *Attorney, Agent, or Firm* — Knobbe, Martens, Olson & Bear LLP

(57) ABSTRACT

The present invention provides methods of increasing sequencing accuracy. For example, the methods of the invention use linear amplification to generate a relatively small population of template molecules that may be subsequently amplified into a larger clonal population of DNA molecules for sequencing.

11 Claims, 14 Drawing Sheets

(56) References Cited

U.S. PATENT DOCUMENTS

| | | |
|---|---|---|
| 7,115,400 B1 | 10/2006 | Adessi |
| 7,985,565 B2 | 7/2011 | Mayer |
| 2009/0203085 A1 | 8/2009 | Kurn et al. |
| 2009/0305288 A1 | 12/2009 | Nakamoto |
| 2010/0112558 A1* | 5/2010 | Gao ............ C12Q 1/6834 435/6.11 |
| 2012/0053063 A1 | 3/2012 | Rigatti |
| 2014/0024537 A1 | 1/2014 | Rigatti |

FOREIGN PATENT DOCUMENTS

| | | |
|---|---|---|
| WO | WO 2009/102878 | 8/2009 |
| WO | WO 2011/025477 | 3/2011 |
| WO | WO 2013/117595 | 8/2013 |
| WO | WO 2013/131962 | 9/2013 |

OTHER PUBLICATIONS

Mitra et al., "In situ localized amplification and contact replication of many individual DNA molecules," Nucleic Acids Research, vol. 27, No. 24, e34, pp. i-vi. (Year: 1999).*

Grisedale, et al, Linear amplification of target prior to PCR for improved low template DNA results, BioTechniques (2014) retrieved from the internet: URL: http://www.ncbi.nlm.nih.gov/pubmed/24641479.

Sengupta, et al, Single Read and Paired End mRNA-Seq Illumina Libraries from 10 Nanograms Total RNA, Journal of Visualized Experiments, 56(27) 2011.

Svensen, et al, Microarray Generation of Thousand-Member Oligonucleotide Libraries, PLOS One 6(9):e24906 (2011).

Vilain, et al, Small amplified RNA-SAGE, Methods of Molecular Biology, 258(1):135-152 (2004).

Greene et al, "Transduction of human CD34+ repopulating cells with a self-inactivating lentiviral vector for SCID-X1 produced at clinical scale by a stable cell line" Human Gene Therapy Methods 23:299-300 (2012).

Voigt et al, "Retargeting sleeping beauty transposon insertions by engineered zinc finger DNA-binding domains", Mol Ther, vol. 20:1852-62 (2012).

Search Report issued in Application No. GB1410646.2 dated Mar. 10, 2015.

* cited by examiner

METHODS OF INCREASING SEQUENCING ACCURACY

This application is the U.S. National Phase Entry of PCT. App. No. PCT/GB2015/051736 filed on Jun. 12, 2015 and published in English as WO 2015/189637 on Dec. 17, 2015 which claims the benefit of GB 1410646.2 filed on Jun. 14, 2014, the contents of which are each incorporated by reference in its entirety.

The present invention provides methods of increasing sequencing accuracy. For example, the methods of the invention use linear amplification to generate a typically relatively small population of complementary strands from template molecules wherein the complementary strands generated from a particular template are retained in close proximity to each other, thus correcting errors at a molecule by molecule level. The linearly amplified populations may be subsequently amplified into a larger clonal population of DNA molecules e.g. by exponential amplification for sequencing.

Figure 1:
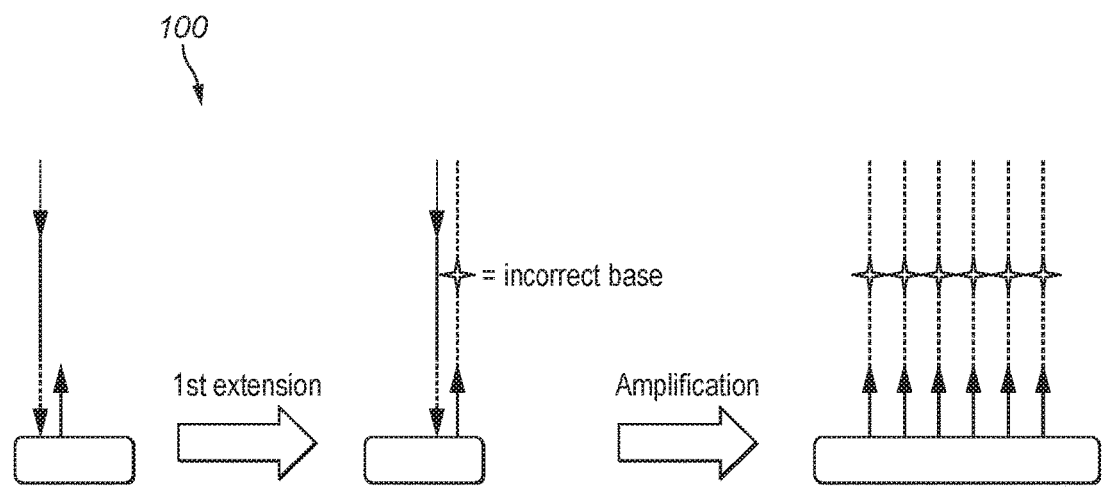

Errors may be introduced into DNA during first extension in a clonal amplification protocol. FIG. 1 shows a schematic diagram 100 of a misincorporation error during first extension. In this example, a DNA molecule is first hybridized to a surface-bound oligonucleotide. The hybridized oligonucleotide is then extended by a DNA polymerase in a step called "first extension." In this example, the polymerase incorporates an incorrect nucleotide at a particular position (the misincorporated base is shown as a cross/star) during the first extension step. After the first extension, an amplification step is implemented that produces multiple copies of the DNA molecule that was generated during first extension. During amplification, the error introduced during the first extension step is propagated in all of the molecules that are part of the clonal population. The misincorporated base will be sequenced as a "high quality error" which may be difficult to distinguish from a bona fide mutation in the sample.

Figure 2:
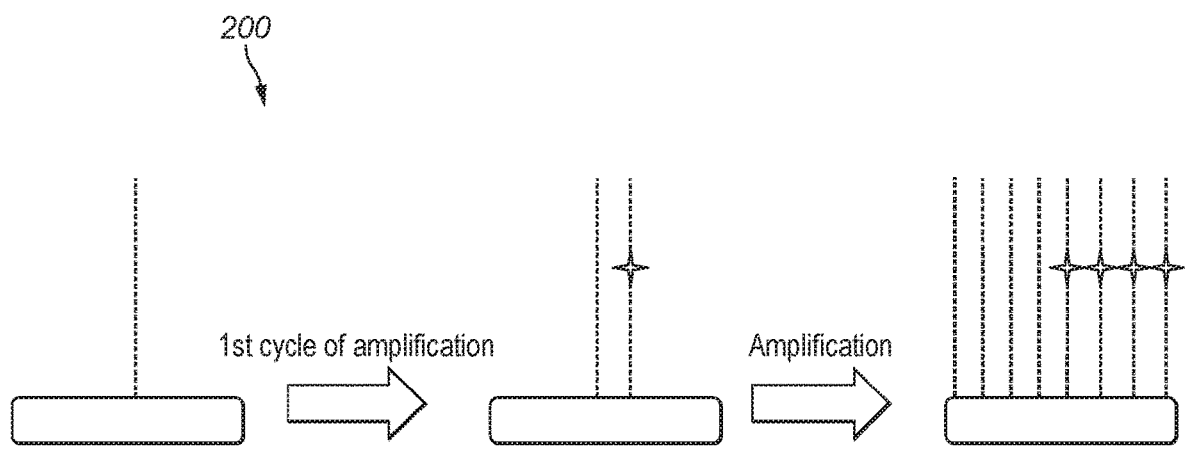

Incorporation errors made in the first or second cycle of the clonal amplification process produce a mixed signal when that particular position is sequenced. FIG. 2 shows a schematic diagram 200 of a misincorporation error during the first cycle of amplification (the misincorporated base is shown as a cross/star). At this early stage, the clonal population is composed of two molecules; one molecule has the correct base, whereas the other carries a misincorporated base. As the clonal amplification process continues, both molecules are used as templates to generate more DNA molecules. The final clonal population may be composed of both wild-type and misincorporated molecules in approximately equal amounts, although stochastic events could skew the ratio. The mixed signal produced by the mixed population of molecules produces a "low quality" base call. The timing (cycle number) at which the misincorporation event occurs, together with stochastic effects occurring in early cycles of amplification, will influence the proportion of wild-type and mutant molecules that are present in a particular clonal population.

In one embodiment, the method of the invention may be used to substantially reduce or eliminate high quality errors that may be generated during first extension.

In another embodiment, the methods of the invention may also be used to reduce errors caused by mis-incorporation of nucleotides during the first few cycles of amplification.

According to the present invention there is provided a method of sequencing with improved accuracy comprising; providing a nucleic acid template; producing, by linear amplification directly from the template nucleic acid, a population comprising a plurality of complementary strands retained in close proximity to each other or identifiable as being obtained from the same template nucleic acid; and performing a sequencing reaction on said proximity retained (e.g. surface bound) oligonucleotides.

Preferably there are a least three rounds of linear amplification.

By having a minimum number of three rounds of linear amplification the effects of any introduced errors will be diluted compared to typical exponential amplification methods. For example, if we assume that starting from an ssDNA strand A on the surface, that linear amplification just makes a copy A' at each round, while exponential amplification makes A' in the $1^{st}$ round, but then both A and A' in subsequent rounds, then a mistake made in making A' at the $1^{st}$ round would result in the A' strands being 100% wrong at round 1 (for both amplifications), 50% wrong at round 2 (for both amplifications) but then at round 3 only ⅓ of the A' strands has a mistake in linear amplification, but for exponential amplification ⅔ of the A' strands has a mistake. After this, using exponential amplification continues to make 50% of the A' strands with a mistake, while with the present method, using linear amplification of the nucleic acid template, the mistake gets ever more diluted. The following example shows a comparison of error propagation for linear amplification and exponential amplification, where A and A' denoted the strands being made, and bold and underlined indicates a mutation containing strand.

| Round Seeding | Linear amplification A | Exponential amplification A |
|---|---|---|
| 1 | A A' | A A' |
| 2 | A A' A' | A A' A A' |
| 3 | A A' A' A' | A A' A A' A A' A A' |
| 4 | A A' A' A' A' | A A' A A' A A' A A' <br> A A' A A' A A' A A' |

Preferably the method further comprises the step of carrying out further (exponential) amplification of the population of complementary strands after the rounds of linear amplification and prior to performing the sequencing reaction.

Optionally, the population comprising a plurality of complementary strands obtained by linear amplification directly from the template nucleic acid are retained in close proximity to each other as they are bound to a surface.

Alternatively the population comprising a plurality of complementary strands obtained by linear amplification directly from the template nucleic acid are retained in close proximity to each other as they are retained in a gel or an emulsion which prevents or limits diffusion.

Preferably, a plurality of nucleic acid templates are provided and a plurality of populations of complementary strands are produced with each population being derived directly from a template and the members of each template derived population being retained in close proximity to each other.

Advantageously, by creating molecules by linear amplification of a particular surface bound library molecule prior to clonal amplification, the molecules created by said linear amplification remain in close proximity. Surface binding in this manner leads very easily to further sequencing steps. The retention of populations of linearly amplified molecules derived from the same template in close proximity can also be achieved by hybridising or attaching the amplified molecules after linear amplification e.g. if rolling circular amplification is used. Retention in close proximity can also be achieved by carrying out the linear amplification rounds inside a gel or an emulsion to prevent free diffusion. This allows the dilution effect to be exploited such that any mis-incorporation error will get diluted out (as it is extremely unlikely that two molecules in the population of complementary strands created by linear amplification will carry the same mutation). Whilst the linear amplification step entirely in solution (i.e. without retention of complementary strands in close proximity for a population obtained directly from the same nucleic acid template) would reduce overall error rates it would still result in "high quality errors" being carried through as a mis-incorporation step (whether in the in solution linear amplification step or in an exponential amplification step) in such a situation would result in a cluster carrying the mutation. The present method allows discrimination between artefacts due to extension errors, as they get diluted out during (surface bound or otherwise proximity retained or diffusion limited) linear amplification and real mutations in the sample itself.

Optionally the method includes the step of attaching the nucleic acid template to the surface. This may be by hybridising said nucleic acid template to a first primer located on the surface. Alternatively the template nucleic acid may be attached directly to the surface.

Preferably the further amplification of the population of complementary strands utilises further amplification primers attached to the surface, said further amplification primers not having been involved in the linear amplification steps.

Optionally the linear amplification (directly from the nucleic acid template) includes the steps of;
hybridising said nucleic acid template to a first primer;
extending the first primer to produce a complementary strand to the template;
denaturing to release the complementary strand which remains in close proximity (e.g. it remains bound to the surface and thus does not travel at all or does not diffuse far before re-hybridising nearby); and
repeating the hybridisation and amplification steps to produce a population of surface bound complementary strands obtained directly from the template nucleic acid.

Optionally the linear amplification could use recombinase polymerase amplification (RPA).

Optionally the linear amplification could use "Wildfire™" (Life Technologies) type amplification to make linear copies of a template strand by a template walking process.

Preferably the clonal amplification step is bridge amplification.

Preferably the method includes the step of sequencing.

Optionally the first primer is bound to a solid support.

Preferably the solid support is a planar element.

Preferably the solid support is a flow cell.

Optionally the solid support is a bead.

Alternatively the single stranded template nucleic acid is circularised prior to being attached to the surface of the solid support e.g. by hybridisation.

Circularisation may use a circligase.

Rolling circular amplification (RCA) results in a concatemer of complementary strands obtained directly from the template nucleic acid.

Preferably the concatemer is then bound to a solid support.

Preferably the solid support comprises a plurality of second primers or fragments thereof.

Fragments of the second primer are not of sufficient size to allow for direct extension under conditions used in the linear amplification step.

Preferably the method includes the step of hybridising reverse complement oligonucleotides to second primer fragments wherein said reverse complement oligonucleotides comprise additional bases at their 5' end that are part of the full length second primer sequence.

The hybridised primers are copied in order to elongate the surface primers thus making them suitable for further use in e.g. exponential amplification.

Optionally the second primers or fragments thereof are grafted onto attachment points.

Grafting may be via a streptavidin/biotin linkage or by streptavidin/dual biotin linkage.

Optionally only about one-half of grafting sites on the solid support are occupied by first primers.

There could alternatively be a skewed ratio.

Optionally the grafting process may be controlled by oligonucleotide concentration, incubation time, and/or temperature.

Preferably second primers are subsequently grafted onto the remaining available grafting attachment points.

Grafting may be by using thiophosphate or click chemistry

Click chemistry includes other chemistries that may be used quickly and reliably to join small units together.

Optionally, linear amplification steps may be carried out at a temperature significantly above the melting temperature (Tm) of the second primers or fragments thereof and the second part of the amplification is performed at a temperature which is below the Tm of the second primers.

Optionally when bound to a solid support at least some of the first primers are blocked.

Such primers can then be unblocked after at least initial linear amplification rounds using standard techniques and can be used for further amplification rounds.

According to a further aspect there is provided a method of sequencing comprising the linear amplification steps of the first aspect.

Figure 3:
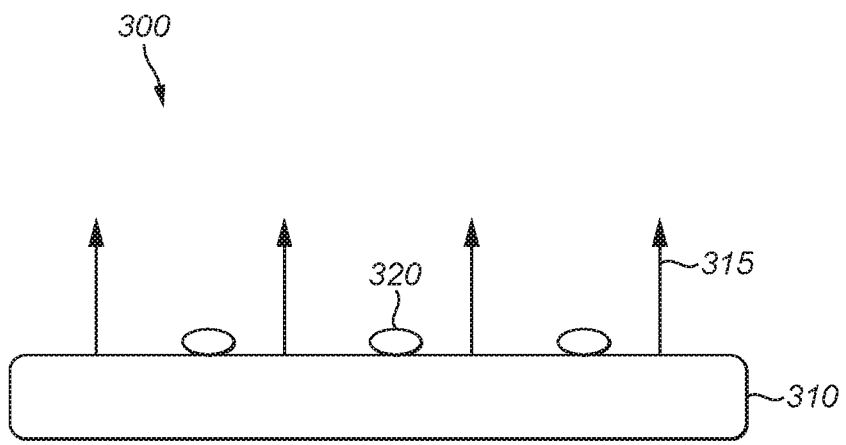
Figure 4:
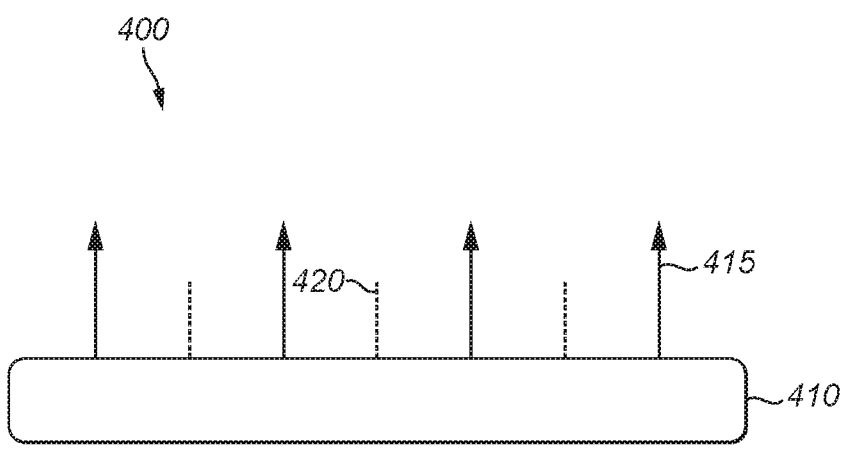
Figure 7A:
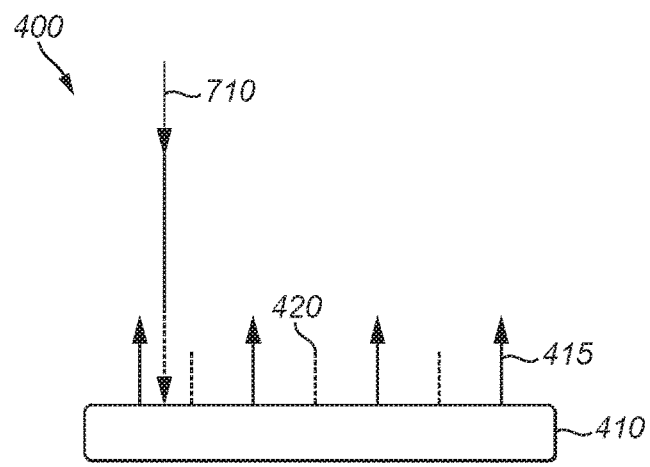
Figure 7B:
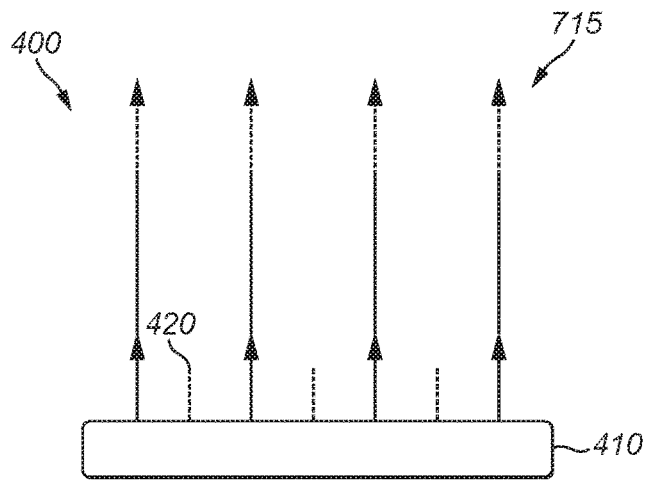
Figure 7C:
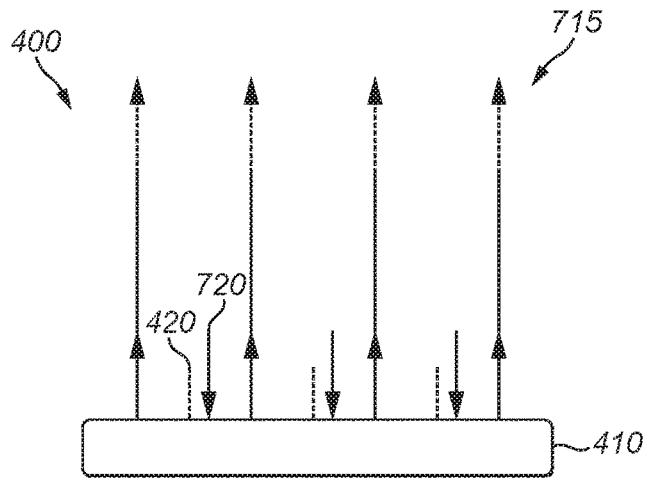
Figure 7D:
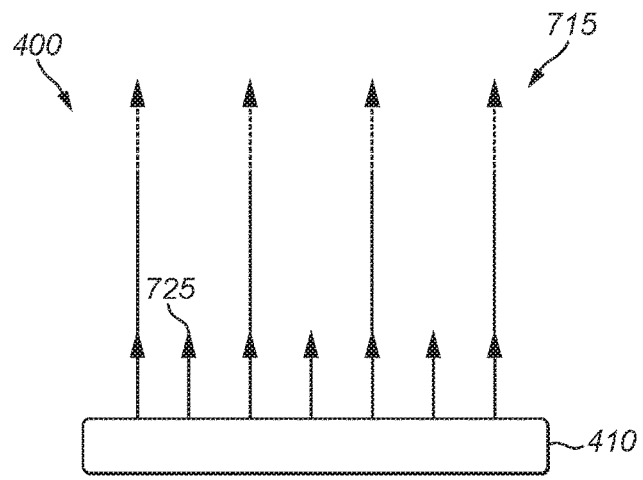
Figure 7E:
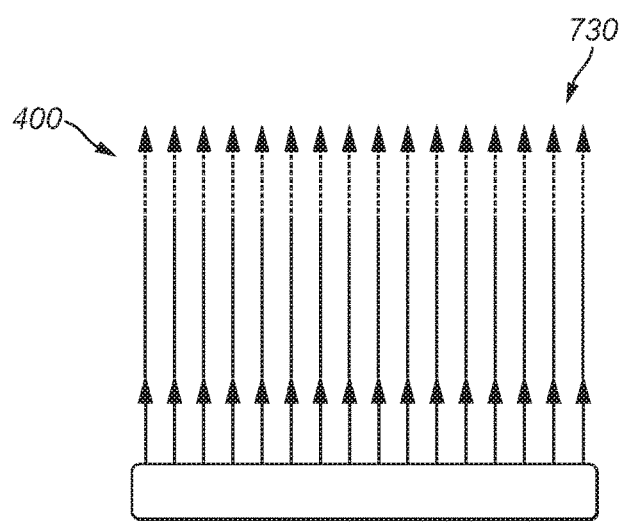
Figure 8A:
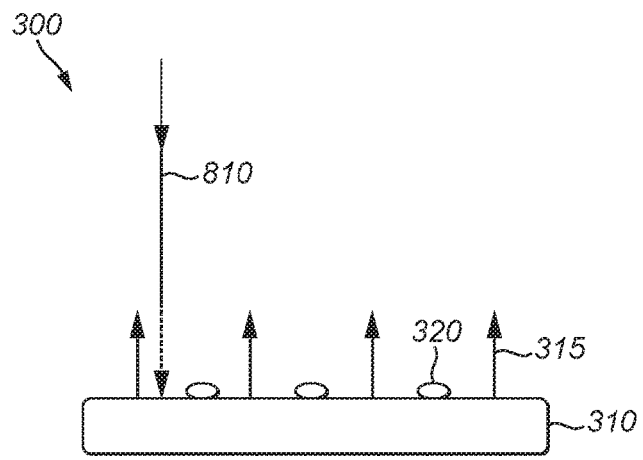
Figure 8B:
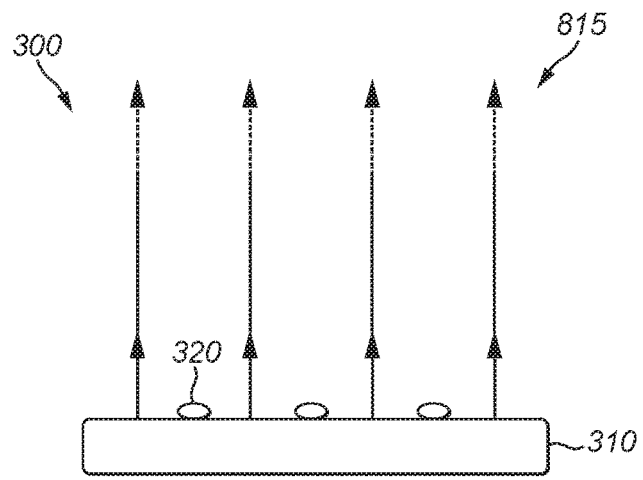
Figure 8C:
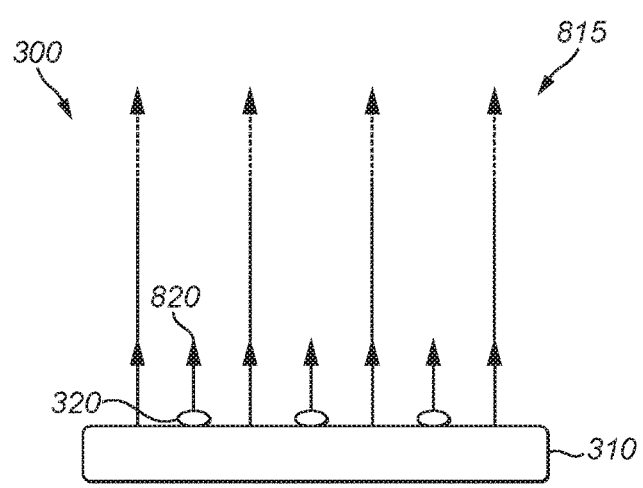
Figure 8D:
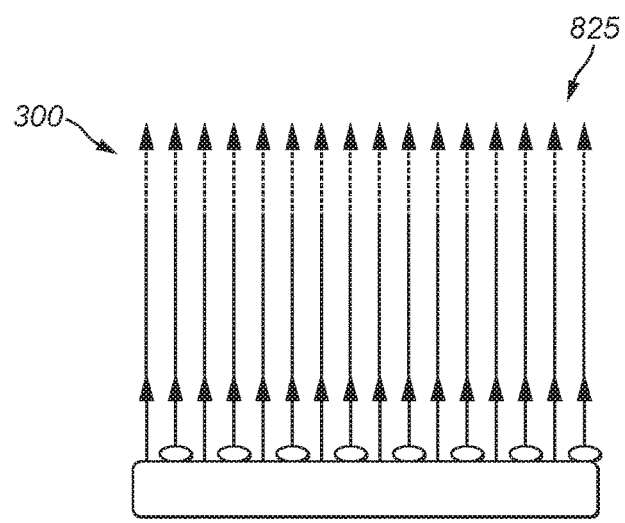
Figure 9A:
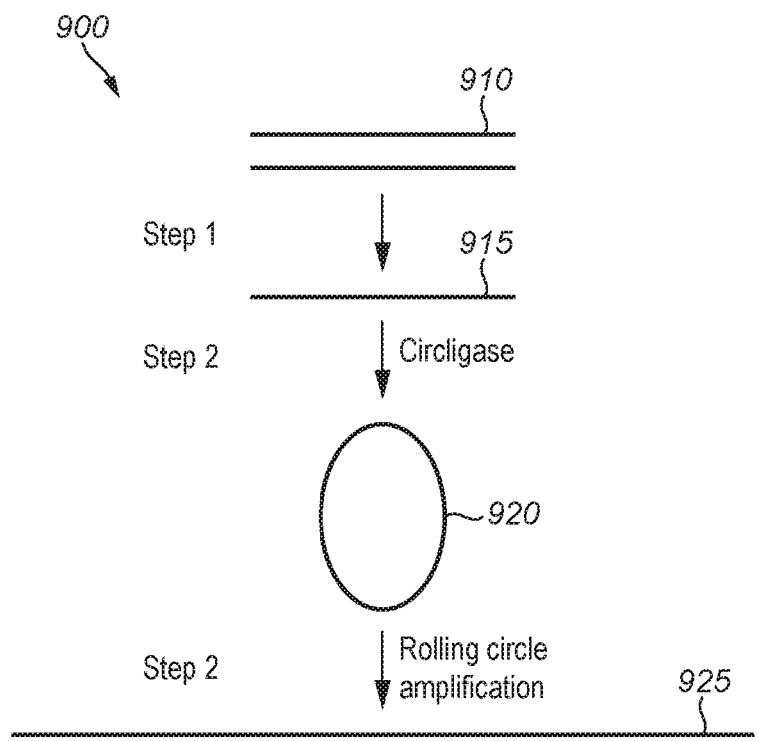
Figure 9B:
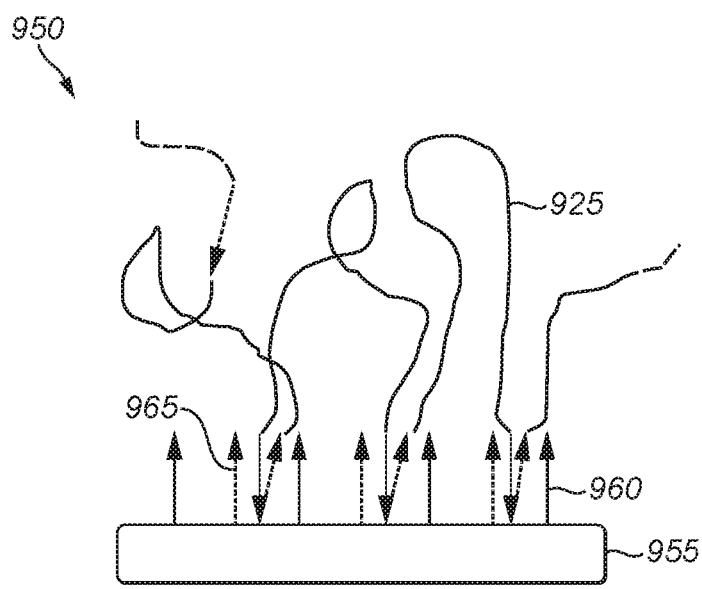
Figure 10A:
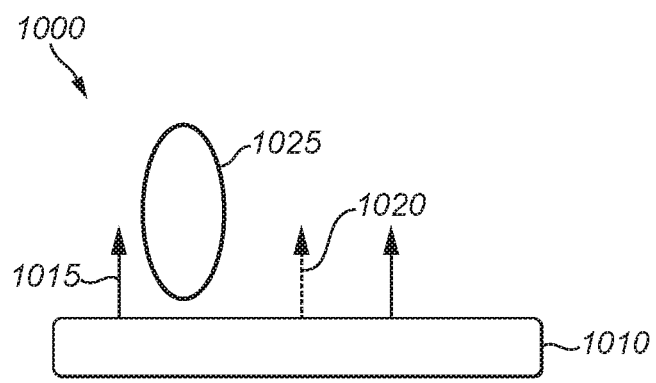
Figure 10B:
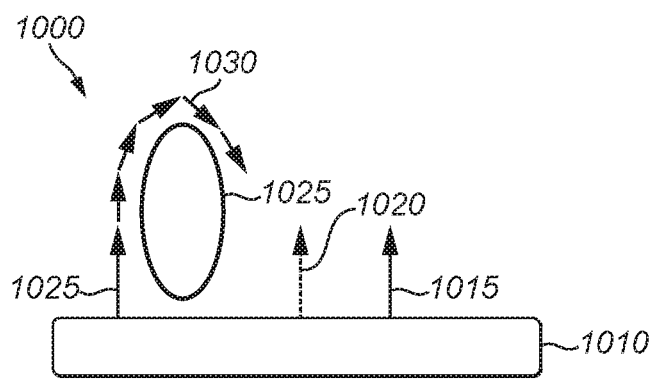
Figure 10C:
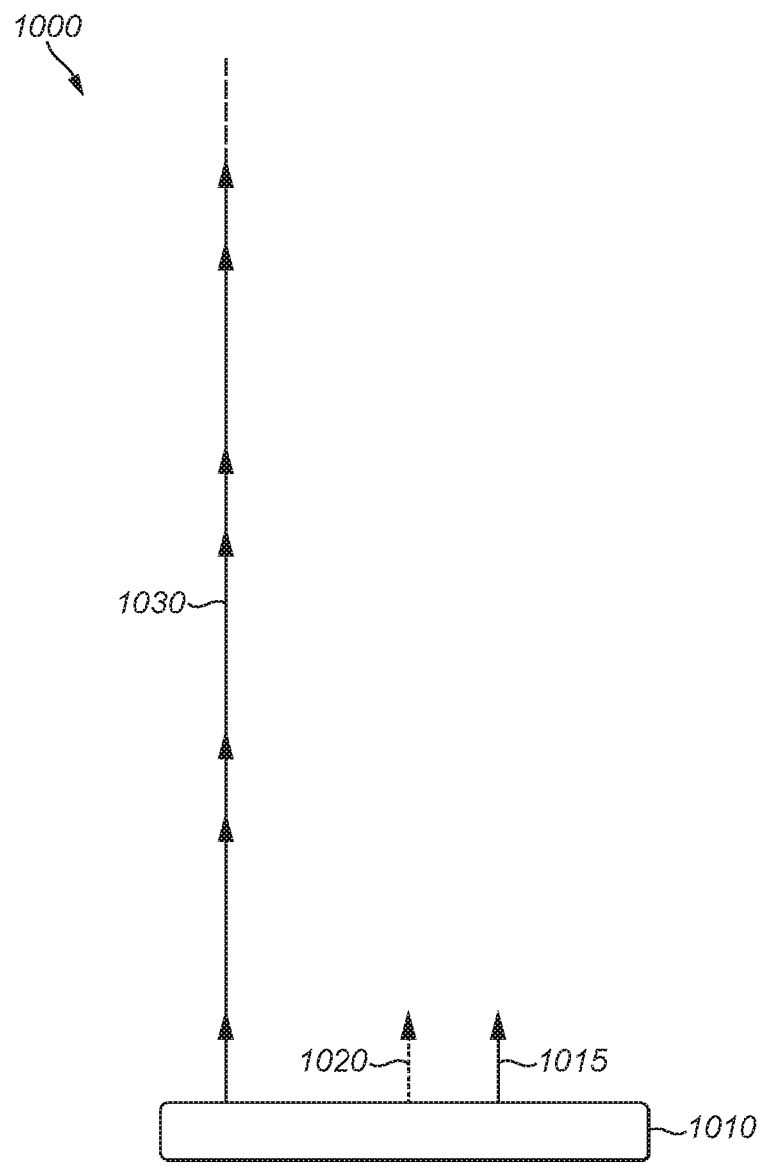

In order to provide a better understanding of the present invention, embodiments will be described, by way of example only and with reference to the following drawings in which;

FIG. 1 shows a schematic diagram of a misincorporation error during first extension; and FIG. 2 shows a schematic diagram of a misincorporation error during the first cycle of amplification; and FIG. 3 illustrates a side view of an example of a portion of a sequencing structure for increased accuracy in high throughput sequencing; and FIG. 4 illustrates a side view of another example of a portion of a sequencing structure for increased accuracy in high throughput sequencing; and FIGS. 5A through 5F illustrate side views of the sequencing structure of FIG. 4 and show an example of a process of forming a small clonal population of DNA molecules by linear amplification; and FIGS. 6A through 6F illustrate side views of the sequencing structure of FIG. 4 and show an example of dilution of DNA polymerase errors by linear amplification; and FIGS. 7A through 7E illustrate side views of the sequencing structure of FIG. 4 and show an example of a process of converting short P7 oligonucleotide primers to full length primers by extension with a polymerase; and FIGS. 8A through 8D illustrate side views of the sequencing structure of FIG. 3 and show an example of a process of attaching a second oligonucleotide primer to a flow cell after linear amplification; and FIG. 9A illustrates an example of a process of linearly amplifying a library by rolling circle amplification (RCA); and FIG. 9B illustrate a side view of a sequencing structure and shows an example of a process of seeding concatemer DNA molecule of FIG. 9A onto a flow cell;

FIGS. 10A through 10C illustrate side views of a sequencing structure and show an example of a process of linearly amplifying circular library molecules directly on a flow cell; and FIGS. 11A through 11E illustrate side views of a sequencing structure and show an example of a process of ligating library molecules onto a flow cell via a splint oligonucleotide for linear amplification.

In certain non-illustrated embodiments, the methods of the invention use a gel or emulsion to prevent significant diffusion of populations of complementary strands formed by linear amplification of specific template nucleic acids/library molecules.

In various embodiments, the methods of the invention use a solid surface that comprises a single "full length" surface-bound oligonucleotide primer (e.g., full length P5 primers) and linear amplification to produce a small clonal population of DNA molecules.

FIG. 3 illustrates a side view of an example of a portion of a sequencing structure 300 for increased accuracy in high throughput sequencing. Sequencing structure 300 includes a solid support 310. In one example, solid support 310 is a planar structure, such as a flow cell. In another example, solid support 310 is a bead (not shown). A plurality of full length P5 oligonucleotide primers 315 may be bound to the surface of sequencing structure 300. A plurality of attachment points 320 for attachment of P7 oligonucleotide primers may be bound to the surface of solid support 310. Attachment points 320 may be used, for example, to attach full length P7 oligonucleotide primers to solid support 310 after a linear amplification step as described in more detail with reference to FIGS. 8A through 8D.

FIG. 4 illustrates a side view of an example of a portion of a sequencing structure 400 for increased accuracy in high throughput sequencing. Sequencing structure 400 includes a solid support 410 and a plurality of full length P5 oligonucleotide primers 415. Sequencing structure 400 also includes a plurality of short P7 oligonucleotide primers 420. Short P7 oligonucleotide primers 420 are not of sufficient length to support amplification, but may be extended at a later step in an amplification protocol. In one example, short P7 oligonucleotide primers 420 may be extended by hybridizing a longer reverse complementary oligonucleotide to short P7 oligonucleotide primers 420 and extending short P7 oligonucleotide primers 420 with a DNA polymerase and dNTPs (not shown). This primer extension step may be performed after a linear amplification step as described in more detail herein below with reference to FIGS. 7A through 7E. Alternatively, the linear amplification step may be carried out at a temperature significantly above the melting temperature (Tm) of short P7 oligonucleotide primers 420 and the second part of the amplification is performed at a temperature which is below the Tm of short P7 oligonucleotide primers 420. Because the second part of the amplification is performed at a temperature that is below the Tm of short P7 oligonucleotide primers 420, short P7 oligonucleotide primers 420 may participate in the amplification process.

FIGS. 5A through 5F illustrate side views of sequencing structure 400 of FIG. 4 and show an example of a process of forming a small clonal population of DNA molecules by linear amplification. An example of a process of forming a small clonal population of DNA molecules by linear amplification may include, but is not limited to, the following steps.

Figure 5A:
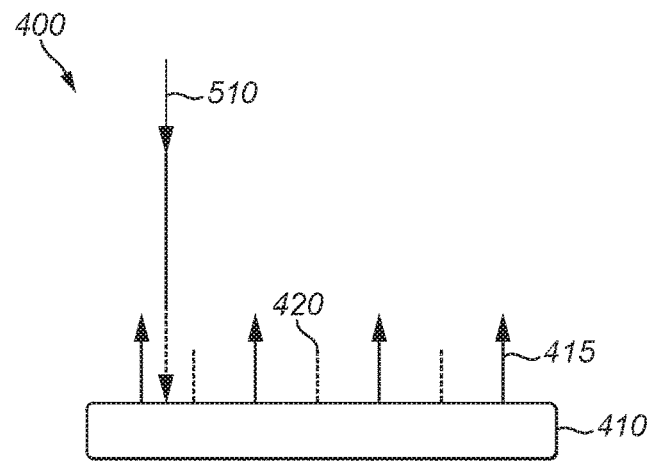

In one step, FIG. 5A shows hybridization of a seeded DNA molecule 510 to P5 oligonucleotide primer 415.

Figure 5B:
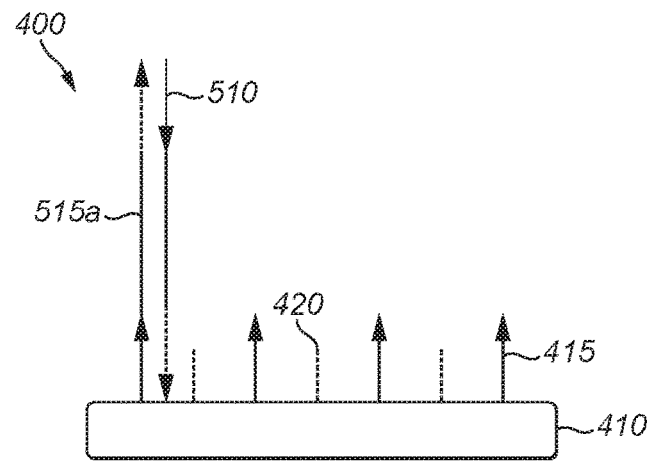

In another step, FIG. 5B shows extension of P5 oligonucleotide primer 415 to produce a complementary strand 515a. Complementary strand 515a is bound to the surface of solid support 410 via P5 oligonucleotide primer 415.

Figure 5C:
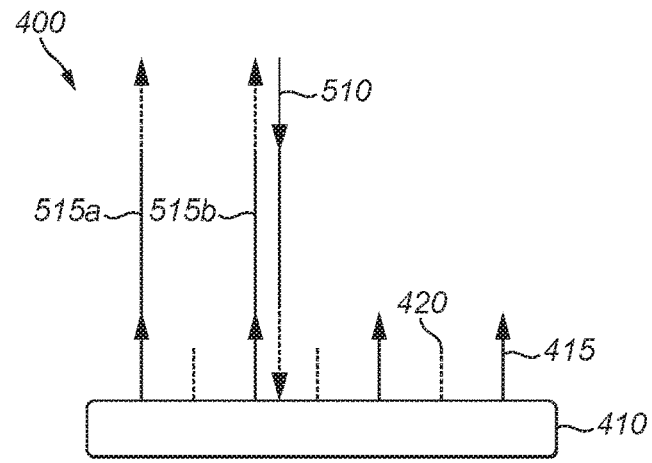

In another step, FIG. 5C shows hybridization of seeded DNA molecule 510 to a second P5 oligonucleotide primer in a second amplification cycle (e.g., denaturation, annealing, and extension). The second P5 oligonucleotide primer 415 is extended to produce a second complementary strand 515b. Complementary strand 515b is also bound to the surface of solid support 410 via P5 oligonucleotide primer 415.

Figure 5D:
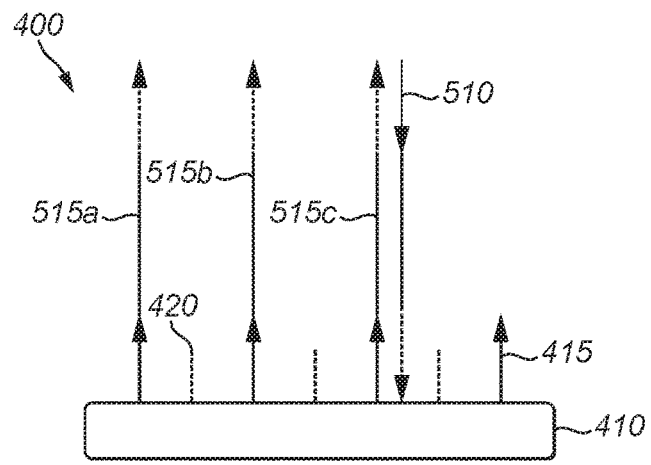

In another step, FIG. 5D shows hybridization of seeded DNA molecule 510 to a third P5 oligonucleotide primer in a third amplification cycle (e.g., denaturation, annealing, and extension). The third P5 oligonucleotide primer 415 is extended to produce a third complementary strand 515c. Complementary strand 515c is also bound to the surface of solid support 410 via P5 oligonucleotide primer 415.

Figure 5E:
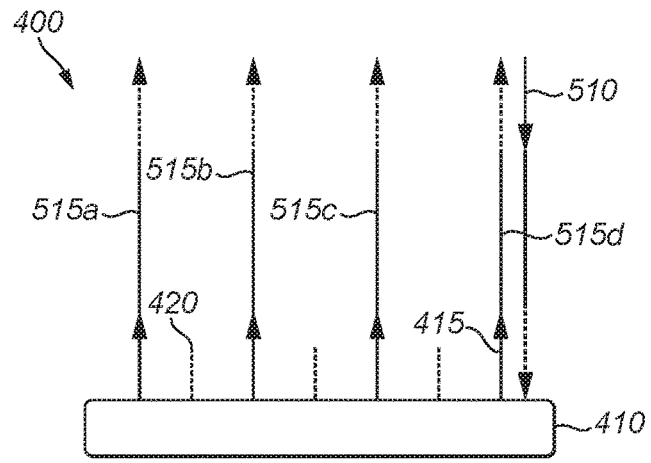

In another step, FIG. 5E shows hybridization of seeded DNA molecule 510 to a fourth P5 oligonucleotide primer in a fourth amplification cycle (e.g., denaturation, annealing, and extension). The fourth P5 oligonucleotide primer 415 is extended to produce a fourth complementary strand 515d. Complementary strand 515d is also bound to the surface of solid support 410 via P5 oligonucleotide primer 415. The amplification process may be repeated any number of times. In one example, the linear amplification process is repeated for 10 cycles.

Figure 5F:
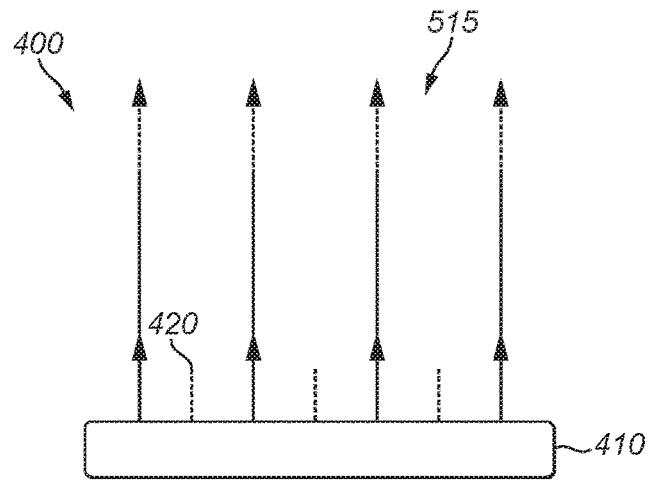

In another step, FIG. 5F shows removal of seeded DNA template 510 at the completion of the desired number of amplification cycles. A small population of complementary strands 515 remains bound to solid support 410. Numerous unused P5 oligonucleotide primers 415 may also be present on the surface of solid support 410 after completion of the linear amplification process (not shown).

In the linear amplification process, only the original seeded DNA molecules are used as templates to produce new molecules. Because only the original seeded DNA molecules are used as templates, errors that may be introduced during linear amplification do not get propagated. For example, the likelihood of introducing the same error at the same position in all of the molecules that are part of a small clonal population (produced by linear amplification) is extremely low. For example, if the accuracy of the polymerase being used is 99.9% (i.e., one error every 1,000 nucleotides), the probability of getting the same error at the same position in "n" number of molecules is equal to $(0.001)^n$. Therefore, the probability of having a mutation at the same position in two molecules is one in a million and in three molecules is one in a billion. Note that these calculations do not take into account that the mutations introduced could be different from one another. For example, if T is the correct base, one molecule could carry an A whereas another molecule could carry a C mutation. Creation of multiple copies from the original molecule through linear amplification leads to a significant improvement in accuracy, i.e., virtually an error free technology compared to a 0.1% error in a standard amplification procedure that does not include an initial step of linear amplification. The high level of accuracy that can be achieved with the methods described herein is particularly beneficial when performing certain applications. For example, when looking at somatic mutations (i.e. cancer), consensus coverage cannot be used to "weed out" sequencing errors due to mis-incorporation during the first extension and bridge amplification steps. By using this method, one can have greater confidence that a particular SNP is a bona fide somatic mutation and not a mis-incorporation event.

In another example, if an error is introduced during the first round of linear amplification and then an additional nine cycles of linear amplification produce nine more molecules with the correct base, about 90% of the signal will be represented by the correct base. Because 90% of the signal will be represented by the correct base, it may still be possible to call the correct base. In contrast, in a standard clonal amplification protocol (i.e., first extension followed directly by surface amplification with both primers present on the flow cell surface and actively participating in the amplification step), an error in the first cycle of amplification may lead to approximately 50% of the molecules carrying the mutation (although through stochastic effects this percentage could be significantly higher). Because approximately 50% (or perhaps higher) of the molecules may carry the mutation, it is very difficult to ascertain the correct base.

FIGS. 6A through 6F illustrate side views of sequencing structure 400 of FIG. 4 and show an example of dilution of DNA polymerase errors by linear amplification.

Figure 6A:
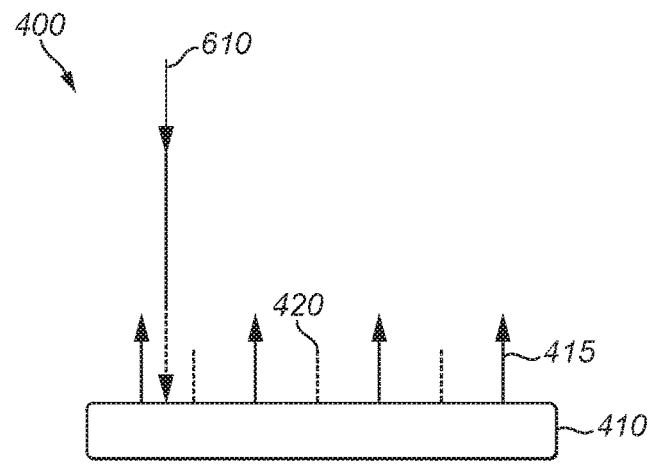

In one step, FIG. 6A shows hybridization of a seeded DNA molecule 610 to P5 oligonucleotide primer 415.

Figure 6B:
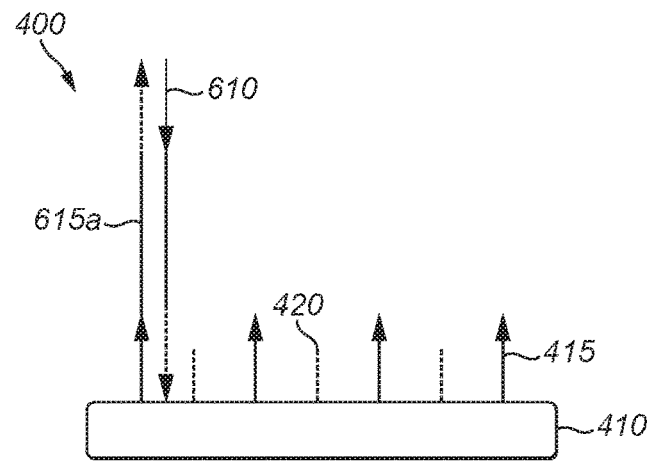

In another step, FIG. 6B shows extension of P5 oligonucleotide primer 415 to produce a complementary strand 615a. Complementary strand 615a is bound to the surface of solid support 410 via P5 oligonucleotide primer 415.

Figure 6C:
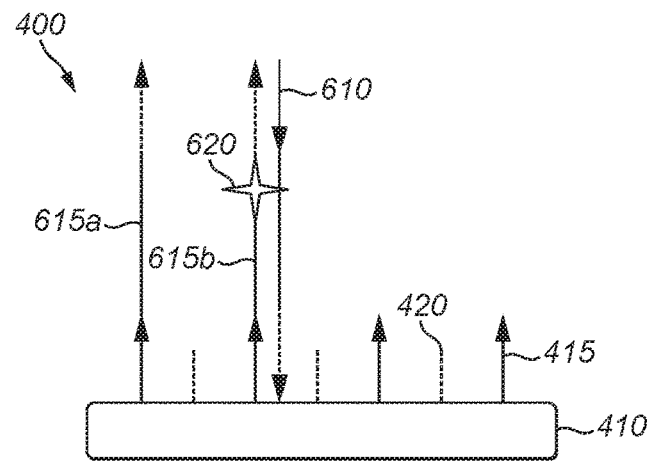

In another step, FIG. 6C shows hybridization of seeded DNA molecule 610 to a second P5 oligonucleotide primer in a second linear amplification cycle (e.g., denaturation, annealing, and extension). The second P5 oligonucleotide primer 415 is extended to produce a second complementary strand 615b. During the second extension, a misincorporation error 620 is introduced by DNA polymerase. Complementary strand 615b is also bound the surface of solid support 410 via P5 oligonucleotide primer 415. Because short P7 oligonucleotide primers 420 are not of sufficient length to support amplification, strand 615b with error 620 therein cannot participate in the amplification process and error 620 is not propagated. All other amplified strands 615, i.e., 615a, 615c, and 615d have the correct nucleotide at that particular location.

Figure 6D:
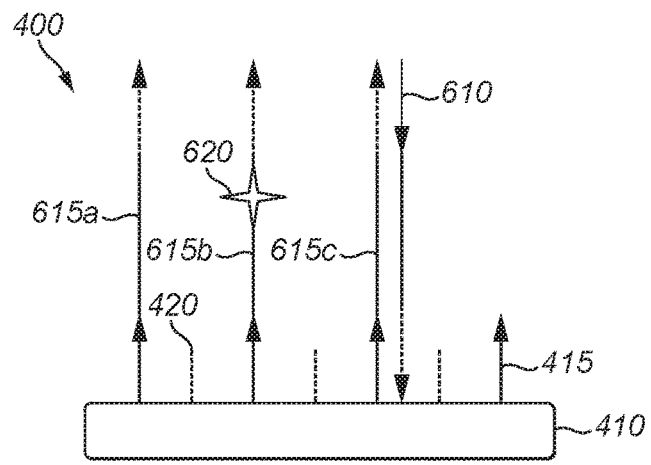

In another step, FIG. 6D shows hybridization of seeded DNA molecule 610 to a third P5 oligonucleotide primer in a third linear amplification cycle (e.g., denaturation, annealing, and extension). The third P5 oligonucleotide primer 415 is extended to produce a third complementary strand 615c. Complementary strand 615c is also bound to the surface of solid support 410 via P5 oligonucleotide primer 415. Because short P7 oligonucleotide primers 420 are not of sufficient length to support amplification, strand 615b with error 620 therein cannot participate in the amplification process and error 620 is not propagated. All other amplified strands 615, i.e., 615a, 615c, and 615d have the correct nucleotide at that particular location.

Figure 6E:
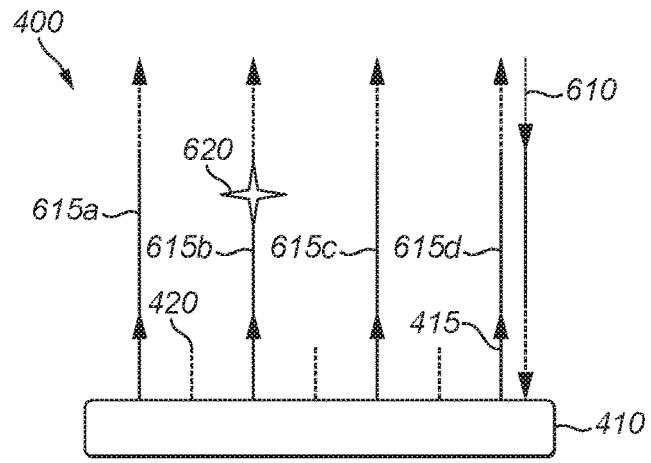

In another step, FIG. 6E shows hybridization of seeded DNA molecule 610 to a fourth P5 oligonucleotide primer in a fourth linear amplification cycle (e.g., denaturation, annealing, and extension). The fourth P5 oligonucleotide primer 415 is extended to produce a fourth complementary strand 615d. Complementary strand 615d is also bound the surface of solid support 410 via P5 oligonucleotide primer 415. Again, because short P7 oligonucleotide primers 420 are not of sufficient length to support amplification, strand 615b with error 620 therein cannot participate in the amplification process and error 620 is not propagated. The amplification process may be repeated any number of times. The number of linear amplification cycles may be selected based on an acceptable level of error. Because, the majority of complementary strands 615 have the correct nucleotide sequence at any particular position, a correct base call during sequencing may be made.

Figure 6F:
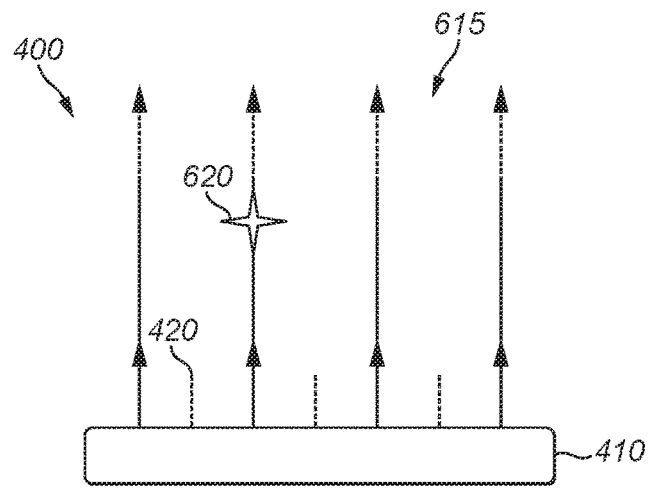

In another step, FIG. 6F shows removal of seeded DNA template 610 at the completion of the desired number of linear amplification cycles. A small population of complementary strands 615 remains bound to solid support 410.

A small clonal population of complementary strands generated by linear amplification on a flow cell surface comprising short P7 oligonucleotide primers may be further amplified after converting the short P7 oligonucleotide primers to full length primers. Alternatively, further amplification cycles can be carried out at lower temperature that enables the short P7 primers to participate in the amplification process as described previously.

FIGS. 7A through 7E illustrate side views of sequencing structure 400 of FIG. 4 and show an example of a process of converting short P7 oligonucleotide primers 420 to full length primers by extension with a polymerase. An example of a process of converting short P7 oligonucleotide primers 420 by extension may include, but is not limited to, the following steps. In one step, FIG. 7A shows hybridization of a seeded DNA molecule 710 to P5 oligonucleotide primer 415.

In another step, FIG. 7B shows a small clonal population 715 produced by linear amplification as described with reference to FIGS. 5B through 5F.

In another step, FIG. 7C shows a plurality of reverse complement oligonucleotides 720 that are hybridized to short P7 oligonucleotide primers 420. Reverse complement oligonucleotides 720 comprise additional bases at their 5' end that are part of the full length P7 primer sequence. It is also possible to hybridise oligonucleotides 720, and then hybridize another oligonucleotide to said oligonucleotide 720. Oligonucleotide primers 420 and additional oligonucleotides can then be ligated together to give a longer P7 surface oligonucleotide.

In another step, FIG. 7D shows short P7 oligonucleotide primers 420 have been extended by a DNA polymerase to full length oligonucleotide primers 725. Full length oligonucleotide primers 725 may now be used in a bridge amplification process.

In another step, FIG. 7E shows a larger clonal population of DNA molecules 730 generated in a bridge amplification process using full length oligonucleotide primers 725 and extended P5 oligonucleotide primers 415.

FIGS. 8A through 8D illustrate side views of sequencing structure 300 of FIG. 3 and show an example of a process of attaching a second oligonucleotide primer to a flow cell after linear amplification. An example of a process of attaching a second oligonucleotide primer after linear amplification may include, but is not limited to, the following steps.

In one step, FIG. 8A shows hybridization of a seeded DNA molecule 810 to P5 oligonucleotide primer 315.

In another step, FIG. 8B shows a small clonal population 815 produced by linear amplification as described with reference to FIGS. 5B through 5F.

In another step, FIG. 8C shows attachment of a plurality of second P7 oligonucleotide primers 820 to attachment points 320. In one example, P7 oligonucleotide primers 820 are grafted onto attachment points 320 via a streptavidin/biotin linkage (dual biotin could also be used as it is more stable compared to single biotin in terms of its interaction with streptavidin). In this example, attachment points 320 comprise streptavidin and P7 oligonucleotide primers 820 are biotinylated. In another example, the initial grafting of solid support 310 with P5 oligonucleotide primers 315 is controlled such that only about one-half of grafting sites on solid support 310 are occupied by P5 oligonucleotide primers 315. The grafting process may be controlled, for example, by oligonucleotide concentration, incubation time, and/or temperature. P7 oligonucleotide primers 820 are subsequently grafted onto the remaining available grafting sites (e.g., attachment points 320) using thiophosphate or click chemistry (i.e., other chemistries that may be used quickly and reliably join small units together).

In another step, FIG. 8D shows a larger clonal population of DNA molecules 825 generated in a bridge amplification process using grafted oligonucleotide primers 820 and extended P5 oligonucleotide primers 315.

FIG. 9A illustrates an example of a process 900 of linearly amplifying a library by rolling circle amplification (RCA). Process 900 may, for example, be performed in solution. Alternatively, process 900 may be performed directly on a solid surface. As shown in step 1, a double stranded DNA template 910 is denatured to form a single stranded DNA template 915. Double stranded DNA template 910 includes adapter regions that hybridize to P5 and P7 oligonucleotide primer sequences. As shown in step 2, single stranded DNA template 915 is circularized using the enzyme circligase to form a circular DNA template 920. As shown in step 3, circular DNA template 920 is amplified in an RCA process to generate a linear concatemer DNA molecule 925. RCA of circular DNA template 920 generates 10 s-100 s linear copies from the same initial template molecule in concatemer DNA molecule 925. Concatemer DNA molecule 925 may be used to seed cluster growth as described with reference to FIG. 9B. The linear copies are all formed by copying the original circular molecule and therefore any mis-incorporation events happening during the RCA step are not propagated.

FIG. 9B illustrate a side view of a sequencing structure 950 and shows an example of a process of seeding concatemer DNA molecule of FIG. 9A onto a flow cell. Sequencing structure 950 includes a solid support 955. In one example, solid support 955 is a flow cell. Bound on the surface of solid support 955 is a plurality of P5 oligonucleotide primers 960 and a plurality of P7 oligonucleotide primers 965. Concatemer DNA molecule 925 is seeded onto the surface of solid support 955 and hybridizes to P5 oligonucleotide primers 960. Cluster growth is initiated by an initial extension of most if not all linear copies contained in concatemer DNA molecule 925. A standard cluster amplification process may then be used (if required) to provide sufficient material for subsequent sequencing. It is also possible to use a surface with a single type of primer. Clonal populations in this case would be performed by a single extension step of the RCA product.

FIGS. 10A through 10C illustrate side views of a sequencing structure 1000 and show an example of a process of linearly amplifying circular library molecules directly on a flow cell. An example of a process of linearly amplifying circular library molecules directly on a flow cell may include, but is not limited to, the following steps.

In one step, FIG. 10A shows a sequencing structure 1000. Sequencing structure 1000 includes a flow cell 1010. Bound on the surface of flow cell 1010 is a plurality of P5 oligonucleotide primers 1015 and a plurality of P7 oligonucleotide primers 1020. A single stranded circular DNA template 1025 is seeded onto the surface of flow cell 1010 and hybridizes to a P5 oligonucleotide primer 1015.

In another step, FIG. 10B shows linear amplification of circular DNA template 1025 in an RCA process to generate a complementary concatemer DNA molecule 1030.

In another step, FIG. 10C shows concatemer DNA molecule 1030 bound to flow cell 1010 via P5 oligonucleotide primer 1015. In this example, only 3 linearly amplified inserts are shown, but concatemer DNA molecule 1030 may comprise 10 s-100 s of linear copies of the original DNA template. Concatemer DNA molecule 1030 has the repeating structure P5-insert-P7'-P5-insert-P7'-P5-insert-P7'. During the first optional cycle of bridge amplification, concatemer DNA molecule 1030 may hybridize to multiple P7 oligonucleotide primers 1020 (not shown). The P7 oligonucleotide primers 1020 will subsequently be extended to generate P7-insert-P5' strands (and some concatemers thereof too) (not shown). Subsequent cycles of bridge amplification will then proceed as usual, and will tend to favour shorter inserts such that most strands will only contain 1 insert. A standard cluster amplification process may then be used (if required) to provide sufficient material for subsequent sequencing.

FIGS. 11A through 11E illustrate side views of a sequencing structure 1100 and show an example of a process of ligating library molecules onto a flow cell via a splint oligonucleotide for linear amplification. An example of a process of ligating library molecules onto a flow cell via a splint oligonucleotide for linear amplification may include, but is not limited to, the following steps.

Figure 11A:
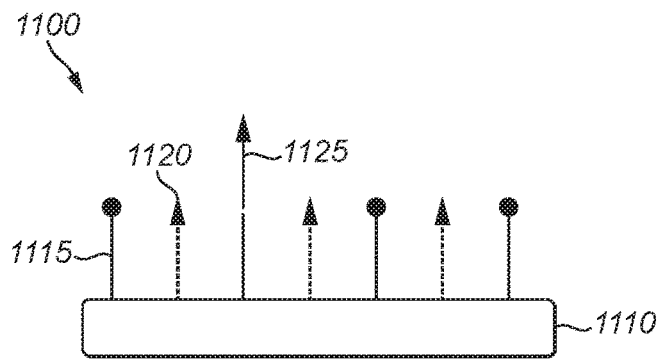

In one step, FIG. 11A shows a sequencing structure 1100. Sequencing structure 1100 includes a flow cell 1110. Bound on the surface of flow cell 1110 are a plurality of blocked P5 oligonucleotide primers 1115, a plurality of P7 oligonucleotide primers 1120, and a plurality of P5 capture primers 1125. In one example, blocked P5 oligonucleotide primers 1115 are 3' phosphate blocked oligonucleotides. In another example, blocked P5 oligonucleotide primers 1115 comprise the 3' reversible block that is present on the fully functional nucleotides used in the Illumina sequencing technology. It is also possible to have short P5 primers of a length selected such that above a certain temperature they cannot participate in the amplification process. These short P5 primers can then be elongated after the linear amplification step has been carried out.

Figure 11B:
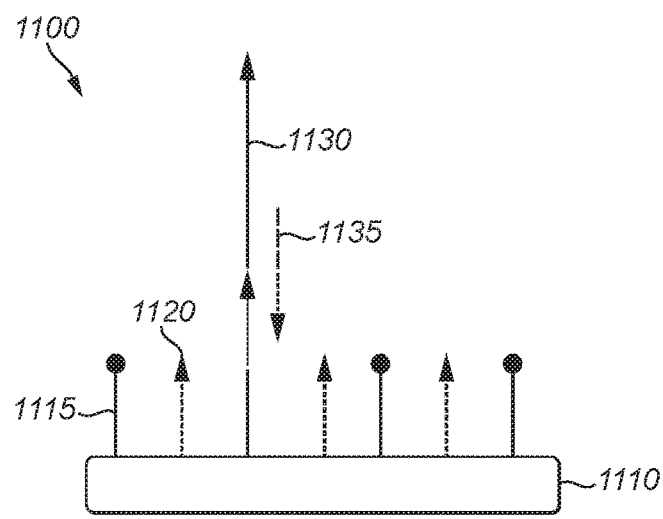

In another step, FIG. 11B shows ligation of a library template molecule 1130 onto P5 capture primer 1125 via a splint oligonucleotide 1135. Library template molecule 1130 does not include sequences that are complementary to blocked oligonucleotide primer 1115. Splint oligonucleotide 1135 includes sequences that are complementary to a portion of library template molecule 1130 and capture primer 1125. Splint oligonucleotide 1135 facilitates the ligation of library template molecule 1130 to P5 capture primer 1125 to form a ligated template molecule 1140.

Figure 11C:
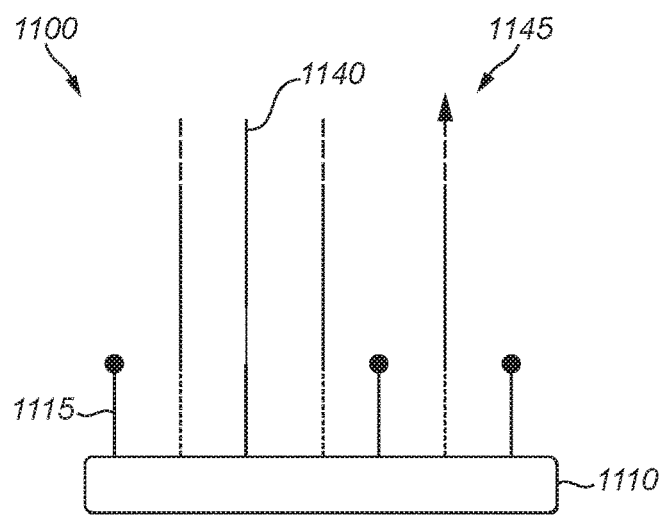

In another step, FIG. 11C shows linear amplification of ligated template molecule 1140 onto surrounding free P7 oligonucleotide primers 1120 to produce linearly amplified molecules 1145.

Figure 11D:
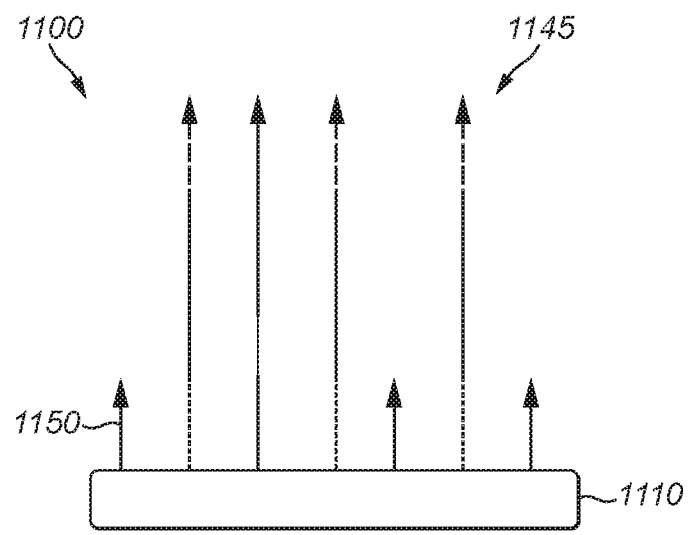

In another step, FIG. 11D shows deblocking of blocked P5 oligonucleotide primers 1115 to yield a plurality of unblocked P5 oligonucleotide primers 1150. In one example, 3' phosphate blocked P5 oligonucleotide primers 1115 are deblocked (i.e., converted to 3' OH) using T4 kinase or phosphatases. Alternatively, if the 3' block is the 3' reversible block that is present on the fully functional nucleotides used in the Illumina sequencing technology, the 3' block may be removed using Illumina's cleavage reagents.

Figure 11E:
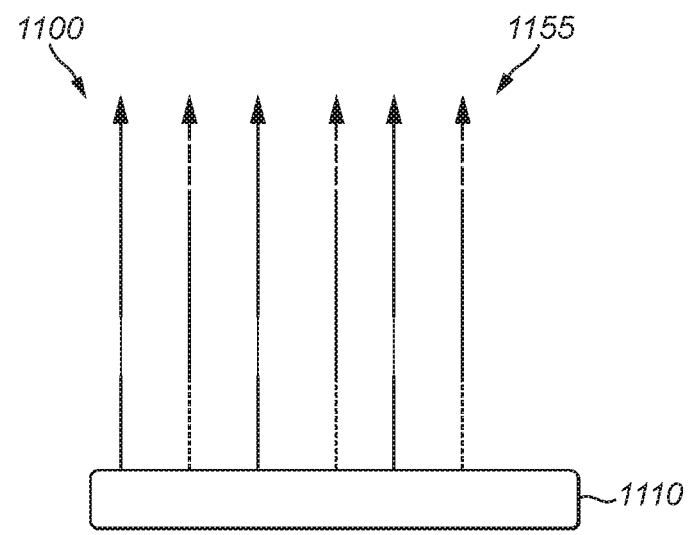

In another step, FIG. 11E shows amplification using a standard cluster amplification process, i.e., a 2 primer-mediated amplification process to generate a clonally amplified population 1155.

In another embodiment of the invention, the solid support may be a bead. In one example, a bead-based linear amplification may be performed in an emulsion to ensure clonality of the amplified population. In another example, individual beads may be seeded in separate nanowells to ensure clonality of the amplified population. In yet another example, the beads may be suspended inside a gel-like solution to prevent or substantially minimize free movement of the beads.

In another embodiment of the invention, linear amplification may be carried out on a bead. Te bead (or beads) may be inside a flow cell during linear amplification, or the linear amplification can occur outside of the flow cell and the bead or beads are flowed into the flow cell after the liner amplification rounds or steps. Nucleic acid (DNA) can then be copied onto the beads to make copies on the surface or alternatively the nucleic acid molecules could be released from the beads using standard techniques and allowed to diffuse slightly on the surface of the flowcell be kept localised in close proximity. Sequencing could be carried out here using known techniques e.g. sequencing by synthesis, or clusters can then be formed i.e. using bridge amplification, (effectively giving clusters formed from and within the original linearly amplified populations) and consensus sequences determined using known sequencing techniques. For example if 10 clusters with the same genomic sequences have a G at position 9 and one has a T it is possible to discard the T and call the base confidently as a G. Sequences can be grouped based on positional information and also on sequence information.

Unique molecular identifiers (UMIs) can also be used in the proposed methods. If UMIs were implemented in the library of template nucleic acids it would be possible to use the UMI information to identify "sister" molecules i.e. molecules that were derived from the same template nucleic acid.

In yet another example, beads could be made to stick to glass wool or metal wool to prevent them from moving around the solution.

The invention claimed is:

1. A method of increasing the accuracy of a sequencing reaction comprising:
providing a nucleic acid template;
providing a surface having a plurality of first primers bound thereto;
producing, by at least three rounds of linear amplification directly from the nucleic acid template, a population comprising a plurality of complementary strands to the nucleic acid template, wherein the population of complementary strands are retained in close proximity to each other and are identifiable as being obtained from the same nucleic acid template, wherein the linear amplification comprises:
  (i) hybridising the nucleic acid template to a primer of the plurality of first primers to produce a hybridized first primer,
  (ii) extending the hybridized first primer to produce a complementary strand to the nucleic acid template,
  (iii) denaturing to release the nucleic acid template which remains in close proximity to the complementary strand, and
  (iv) repeating the hybridising and extending steps to produce the population comprising a plurality of complementary strands obtained directly from the nucleic acid template;
generating a plurality of second primers bound to the surface, wherein the generating is subsequent to the linear amplification;
performing exponential amplification on the population of complementary strands to generate amplified oligonucleotides, comprising:
  (i) hybridizing the population of complementary strands to the second primers to produce hybridized second primers,
  (ii) extending the hybridized second primers to produce extended second primers,
  (iii) hybridizing the extended second primers to the first primers that have not been extended,
  (iv) extending the first primers hybridized to the extended second primers, and
  (v) repeating the hybridizing and extending steps to produce amplified oligonucleotides; and
performing a sequencing reaction on said amplified oligonucleotides.

2. The method of claim 1, wherein a plurality of different nucleic acid templates are provided and a plurality of populations of complementary strands are produced with each population being derived directly from a template and the members of each template derived population being retained in close proximity to each other.

3. The method of claim 1, wherein the exponential amplification of the population of complementary strands is bridge amplification.

4. The method of claim 1, wherein the providing a surface comprises providing a surface comprising a plurality of first primers bound thereto and a plurality of second primer fragments, and the generating comprises:
providing oligonucleotides that are complementary to the second primer sequence along its entire length;
hybridising the oligonucleotides to the second primer fragments; and
extending the second primer fragments to obtain the plurality of second primers bound to the surface.

5. The method of claim 1, wherein the generating a plurality of second primers bound to the surface comprises attaching a plurality of second primers at discrete attachment points on the surface.

6. The method of claim 5, wherein less than or equal to one-half of the attachment points are occupied by the plurality of first primers.

7. The method of claim 6, wherein less than or equal to one half of the attachment points are occupied by the second primers.

8. The method of claim 1, wherein the population of complementary strands identifiable as being obtained from the same template nucleic acid, and the template nucleic acid each comprise a unique molecular identifier (UMI).

9. A method of increasing the accuracy of a sequencing reaction comprising:
  providing a nucleic acid template;
  providing a surface comprising a first primer, and a plurality of second primers or fragments of the second primers;
  producing, by linear amplification directly from the template nucleic acid, a population comprising a plurality of complementary strands to the nucleic acid template, wherein the population of complementary strands are retained in close proximity to each other or identifiable as being obtained from the same template nucleic acid, wherein the linear amplification is carried out at a temperature significantly above the melting temperature (Tm) of the second primers or fragments thereof, wherein the linear amplification comprises:
    hybridizing the nucleic acid template to the first primer,
    extending the first primer to produce a complementary strand to the template,
    denaturing to release the complementary strand which remains in close proximity, and
    repeating the hybridization and extension steps to produce the population of complementary strands obtained directly from the template nucleic acid;
  hybridizing the population of complementary strands to the second primers;
  amplifying the hybridized population of complementary strands; and
  performing a sequencing reaction on the amplified complementary strands.

10. A method of increasing the accuracy of a sequencing reaction comprising:
  providing a nucleic acid template;
  producing, by linear amplification directly from the template nucleic acid, a population comprising a plurality of complementary strands to the nucleic acid template, wherein the population of complementary strands are retained in close proximity to each other or identifiable as being obtained from the same template nucleic acid, wherein the linear amplification comprises:
    hybridizing said nucleic acid template to a first primer of a plurality of first primers,
    extending the first primer to produce a complementary strand to the template,
    denaturing to release the complementary strand which remains in close proximity, and
    repeating the hybridization and extension steps to produce the population of complementary strands obtained directly from the template nucleic acid;
  wherein at least some of the first primers are blocked; and
  performing a sequencing reaction on the population of complementary strands.

11. A method of increasing the accuracy of a sequencing reaction comprising:
  providing a plurality of first primers attached to a solid support;
  performing linear amplification on a template polynucleotide comprising:
    (i) hybridizing the template polynucleotide to a primer of the plurality of first primers,
    (ii) extending the hybridized first primer,
    (iii) removing the template polynucleotide from the extended first primer, and
    (iv) repeating steps (i) (iii) at least three times;
  generating a plurality of extendable second primers attached to the solid support, wherein the generating is performed subsequent to the linear amplification;
  performing exponential amplification on the extended first primers with the extendable second primers; and
  sequencing the amplified extended primers.

* * * * *